US012582523B1

(12) United States Patent
Conti et al.

(10) Patent No.: US 12,582,523 B1
(45) Date of Patent: Mar. 24, 2026

(54) DURABILITY AND PARTICULATE TESTING SYSTEM AND METHOD

(71) Applicants: Christopher Conti, Galena, MO (US); James Conti, Galena, MO (US); Alicia Sullivan, Galena, MO (US); Donald Rohde, Galena, MO (US); Kendra Conti, Galena, MO (US); Elaine Strope, Galena, MO (US)

(72) Inventors: Christopher Conti, Galena, MO (US); James Conti, Galena, MO (US); Alicia Sullivan, Galena, MO (US); Donald Rohde, Galena, MO (US); Kendra Conti, Galena, MO (US); Elaine Strope, Galena, MO (US)

(73) Assignee: DYNATEK LABS, INC., Galena, MO (US)

( * ) Notice: Subject to any disclaimer, the term of this patent is extended or adjusted under 35 U.S.C. 154(b) by 531 days.

(21) Appl. No.: 18/133,406

(22) Filed: Apr. 11, 2023

Related U.S. Application Data

(60) Provisional application No. 63/329,817, filed on Apr. 11, 2022.

(51) Int. Cl.
| | |
|---|---|
| *A61F 2/24* | (2006.01) |
| *G01N 3/56* | (2006.01) |
| *G01N 15/06* | (2006.01) |

(52) U.S. Cl.
CPC ........... *A61F 2/2472* (2013.01); *G01N 3/567* (2013.01); *G01N 15/0618* (2013.01); *A61F 2240/008* (2013.01)

(58) Field of Classification Search
CPC . A61F 2/2472; A61F 2240/008; G01N 3/567; G01N 15/0618
USPC .............. 73/61.71–61.75, 86, 64.56, 863.11, 73/863.33, 865.3, 865.5, 865.6, 866; 356/36, 335, 336, 426–428; 324/71.2, 324/71.4
See application file for complete search history.

(56) References Cited

U.S. PATENT DOCUMENTS

| | | | |
|---|---|---|---|
| 4,546,642 A | 10/1985 | Swanson | |
| 7,621,192 B2 | 11/2009 | Conti et al. | |
| | (Continued) | | |

*Primary Examiner* — Robert R Raevis
(74) *Attorney, Agent, or Firm* — Kutak Rock LLP; James H. Jeffries

(57) ABSTRACT

A medical device durability and particulate testing system is provided including a durability tester component configured for continually actuating movement of structural device(s); a simulated blood fluid; fluid flow lines; a particle counter component configured for recording continuous particulate data from device(s) subjected to durability testing; flow meters; a fluid management system; and one or more system controller(s) having a processor configured with software for controlling operation of the system and recording data. In an embodiment, the system includes a user interface accessible via a display. In some embodiments the system further includes a heater paired with temperature measuring devices to maintain fluid temperatures within appropriate bounds to simulate blood within the body. In an exemplary embodiment, the durability and particulate testing system is a continuous flow, closed loop system and configured for testing synthetic structural heart devices to simulate the expected lifetime of the device(s).

20 Claims, 16 Drawing Sheets

(56) References Cited

U.S. PATENT DOCUMENTS

| | | |
|---|---|---|
| 9,453,788 B2 | 9/2016 | Conti et al. |
| 2014/0216181 A1* | 8/2014 | Conti ..................... G01N 15/02 |
| | | 73/865.5 |

* cited by examiner

120

140

160

120

140

160

DURABILITY AND PARTICULATE TESTING SYSTEM AND METHOD

CROSS-REFERENCE TO RELATED APPLICATIONS

This application claims priority pursuant to 35 U.S.C. 119(e) to U.S. Provisional Patent Application Ser. No. 63/329,817, filed Apr. 11, 2022, the entire disclosure of which is incorporated herein by reference.

FIELD OF THE INVENTION

The present invention relates generally to testing of medical devices. More specifically, the present invention is concerned with a system and method for testing durability and particulate shed of structural heart devices.

BACKGROUND OF THE INVENTION

In modern society, heart disease has become extremely common and can often be life-threatening. In fact, heart diseases are the leading cause of death globally for most demographics. Many types of heart disease can be treated with the implantation of synthetic medical device(s) to replace functional parts of the heart and/or to stabilize the heart and cardiovascular system. Such implantable devices are typically intended for extended, long-term use. Accordingly, materials used for implantable medical devices must be safe to use and effective within the body over extended time periods.

When new devices and/or materials are developed, factors such as durability and degradation of materials of the device must be tested. Implanted structural heart devices are subject to repeated stresses over time as the circulatory system circulates blood throughout the body. For example, heart valves continuously open and close based on directional flow of blood through the heart. Thus, to effectively test the durability of a synthetic heart valve, the synthetic valve must be continually opened and closed, over and over, to simulate actuation over the expected lifetime of the device.

Further, to effectively test for the potential for particulate shed of a synthetic heart valve, particles would need to be counted resulting from the synthetic valve being continuously opened and closed in such a manner to simulate the expected lifetime of the valve. Accordingly, it would be beneficial to have a structural heart device testing system and method configured to continuously actuate the tested device for the expected lifetime of the device and count and record the amount of particulate shed in that time.

Particulate testing is important in order to identify the potential risks of deploying a medical device into a patient. Particles from a medical device can travel through the bloodstream and cause blockages within arteries and/or capillaries. Such blockages greatly increase the likelihood of adverse events such as heart attack, stroke, or death.

While some prior art particulate counting systems and methods are known, currently there are not any other long-term durability particulate testing systems for structural heart devices commercially available. Accordingly, there is a substantial need for particulate testing of surgical accessory devices, heart stents, shunts, occluders, and other endovascular devices.

Pre-existing methods that address this problem include analysis of particulate shed during the tracking and deployment timeframe for the medical device. The particulates are collected, sized, and counted by a light obscuration technique or microscopic visual inspection. Particulates can be captured on capture filters to be analyzed for morphology and chemical characterization. Nevertheless, these methods do not address particulate shed over the expected lifetime of the device. Accordingly, it would be beneficial to have a system and method for testing particulate shed over an expected lifetime of a device.

Clinical ramifications of particle release from structural heart devices are unknown and currently under investigation by regulatory oversight committees. Accordingly, it would be beneficial to have an in vitro test to evaluate device safety before clinical trials.

Heretofore there has not been available a system or method for testing durability and particulate shed of medical devices with the advantages and features of the present invention.

SUMMARY OF THE INVENTION

The present invention comprises a system and method for durability and particulate testing of structural heart devices. In an exemplary embodiment, the present invention is configured for testing synthetic heart valves. In additional embodiments, the present invention is configured for testing occluders, defect closure devices, candidate materials, surgical accessory devices, stents, shunts, other endovascular devices, and combinations thereof. In an exemplary embodiment, the present invention is configured for testing multiple structural heart devices at one time. In an alternative embodiment, the present invention is configured for testing a single structural heart device.

In an exemplary embodiment, the durability and particulate testing system includes a heart structural device durability tester component configured for continually actuating movement of heart structural device(s) being tested; a simulated blood fluid; fluid flow lines; a particle counter component configured for recording continuous particulate data from the structural heart device(s) subjected to durability testing; flow meters to provide proper flow rates; a fluid management system; and one or more system controller(s) having a processor configured with software for controlling operation of the system and recording data. In a preferred embodiment, the system includes a user interface accessible via a display. In some embodiments the system further includes a heater paired with temperature measuring devices to maintain fluid temperatures within appropriate bounds to simulate blood within the body during testing. In addition, in an exemplary embodiment, a pressure pump paired with pressure measuring devices are utilized to subject the test system to certain pressure parameters set by a user. In an exemplary embodiment, the system controller with software of the present invention is configured to control a series of functions including but not limited to operation of motor(s), temperature control, pressure commands, alarm monitoring, and data collection.

In an exemplary embodiment of the present invention, the heart device durability tester component comprises a test unit, a pump unit, and a drive unit. The test unit includes a series of heart device testing chambers arranged in a substantially circular pattern around a central fluid reservoir. The testing unit further includes at least one fluid inflow line into the central fluid reservoir. In an exemplary embodiment, the test unit includes openings from the central fluid reservoir into each of the testing chambers.

In an embodiment, the pump unit comprises a series of bellows. In an exemplary embodiment, the pump unit includes one bellows for each testing chamber. Each bellows is attached to the base of a respective testing chamber and configured for being alternatively compressed and expanded. In an exemplary embodiment, the bellows are attached to a pivotable, disc-shaped swash plate.

In an embodiment, the drive unit of the present invention comprises a drive motor having a rotatable rod. The rotatable rod is connected to a coupling configured for engagement with the swash plate. In an exemplary embodiment, rotation of the rod and slanted coupling is configured for tilting the swash plate in a substantially circular, or oscillating, motion without actual rotation of the swash plate. Such tilting of the swash plate with the motor rotating the rotating rod provides alternating compression and expansion of the bellows.

In an exemplary embodiment of the present invention, the bellows each have one or more outflow fluid line. In an exemplary embodiment, the inflow fluid line is configured to supply a continuous flow of simulated blood fluid into the testing unit central reservoir via a pump fluidically connected from a fluid management system component. The outflow fluid lines are configured to direct fluid from the durability tester component to a particle counting component of the present invention. The durability tester component test unit central fluid reservoir does not include bypass valves. Such lack of bypass valves and the inclusion of outflow fluid lines from the bellows ensure that fluid which has passed through a structural heart device being tested is further directed toward the particle counting component for accurate particle counting in line of the system. Moreover, individual outflow fluid lines running from the bellows below each testing chamber accommodates particle counting for the device in each test chamber. In an exemplary embodiment, the present system allows for multiple trials of the same device to be tested and/or multiple devices to be tested at the same time.

In an exemplary embodiment of the present invention, simulated blood fluid is configured for being continuously pumped through the present invention, and the tilting of the swash plate and resulting alternating compression and expansion of the bellows are configured to actuate movement of the structural heart devices within the testing chambers (e.g., repeatedly open and close synthetic heart valves) and simulate pulsatile flow of blood of the circulatory system.

In exemplary embodiments of the present invention, the pressure and flow rate of fluid through the system can be varied to simulate implantation of the tested devices at different placements within the circulatory system and/or to speed up the timeframe to simulate the expected lifetime duration of the devices. In some embodiments, the outflow fluid lines are bifurcated, trifurcated, or further split between the outflow from durability tester component into the particle counting component. Such splitting of fluid lines can be used to lower the pressure of the fluid flow into the particulate counting mechanism and/or provide for more accurate particle counting.

In an exemplary embodiment, the fluid management system of the present invention is configured to filter out any remaining contaminants within the simulated blood fluid before recirculating the fluid to the durability tester component.

The present invention provides continuous particulate analysis of structural heart devices undergoing durability testing. Particulate data are generated through the simulated (real-time or accelerated) life expectancy (or other specified period of time) of the tested device(s). If degradation of the device occurs, the present system counts and sizes particulates released from the device, providing useful data to determine if the device poses an embolic risk to the patient.

In an embodiment, the present system includes a second controller having a processor configured with software. In such embodiment, one controller is configured for controlling operation of fluid flow and the motor, and the second controller is configured for recording data from particulate counting and sizing. In an exemplary embodiment, the system includes a memory for storing data. In embodiments, the system includes one or more displays configured for displaying data and for allowing a user to customize operation of the system via the user interface.

In an exemplary embodiment, many components of the present system are transparent or translucent, allowing a user to visualize operation of the device during testing. In an exemplary embodiment, testing chambers of the durability tester component are alternated for use and non-use to help prevent potential for cross contamination.

In further embodiments, the durability and particulate testing system comprises capture filter housings for each lane. In an exemplary embodiment, the present system further includes cameras for regular visual monitoring of the testing. In further embodiments, the durability tester component includes individual fluid inflow lines into each testing chamber rather than a central fluid reservoir. In additional embodiments, the testing chambers, bellows, and outflow fluid lines are sectioned off from the other respective sections to prevent cross contamination.

BRIEF DESCRIPTION OF THE DRAWINGS

Embodiments of the present invention are described in detail below with reference to the attached drawing figures, wherein:

FIG. 10 further shows a perspective view of a durability tester component, an elevational view of a particulate counting component, and a perspective view of a fluid management system of the present invention.

Figure 1:
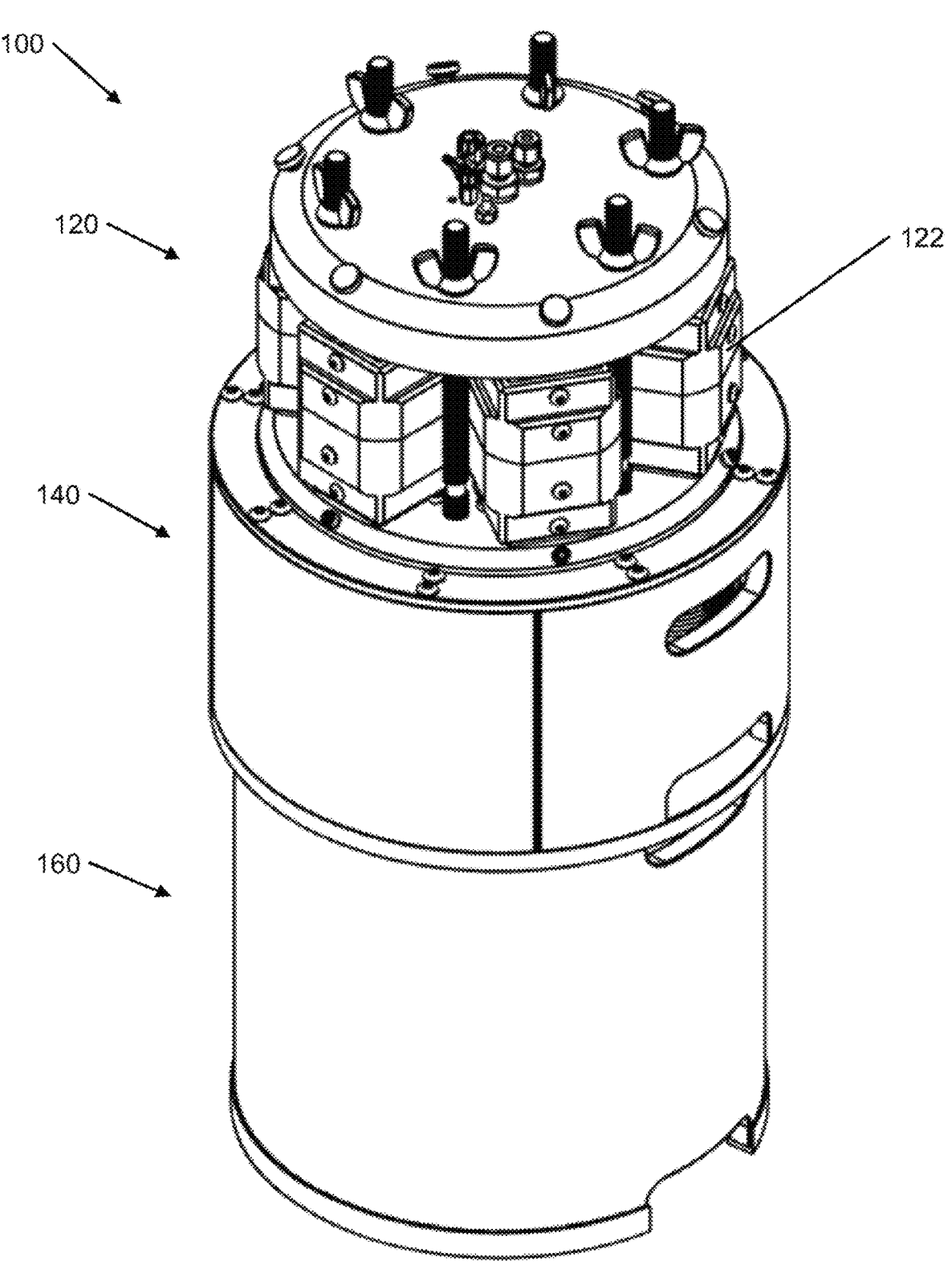
FIG. 1 is an upper, perspective view of a durability tester component of a heart device durability and particulate testing system embodying the present invention.
Figure 2:
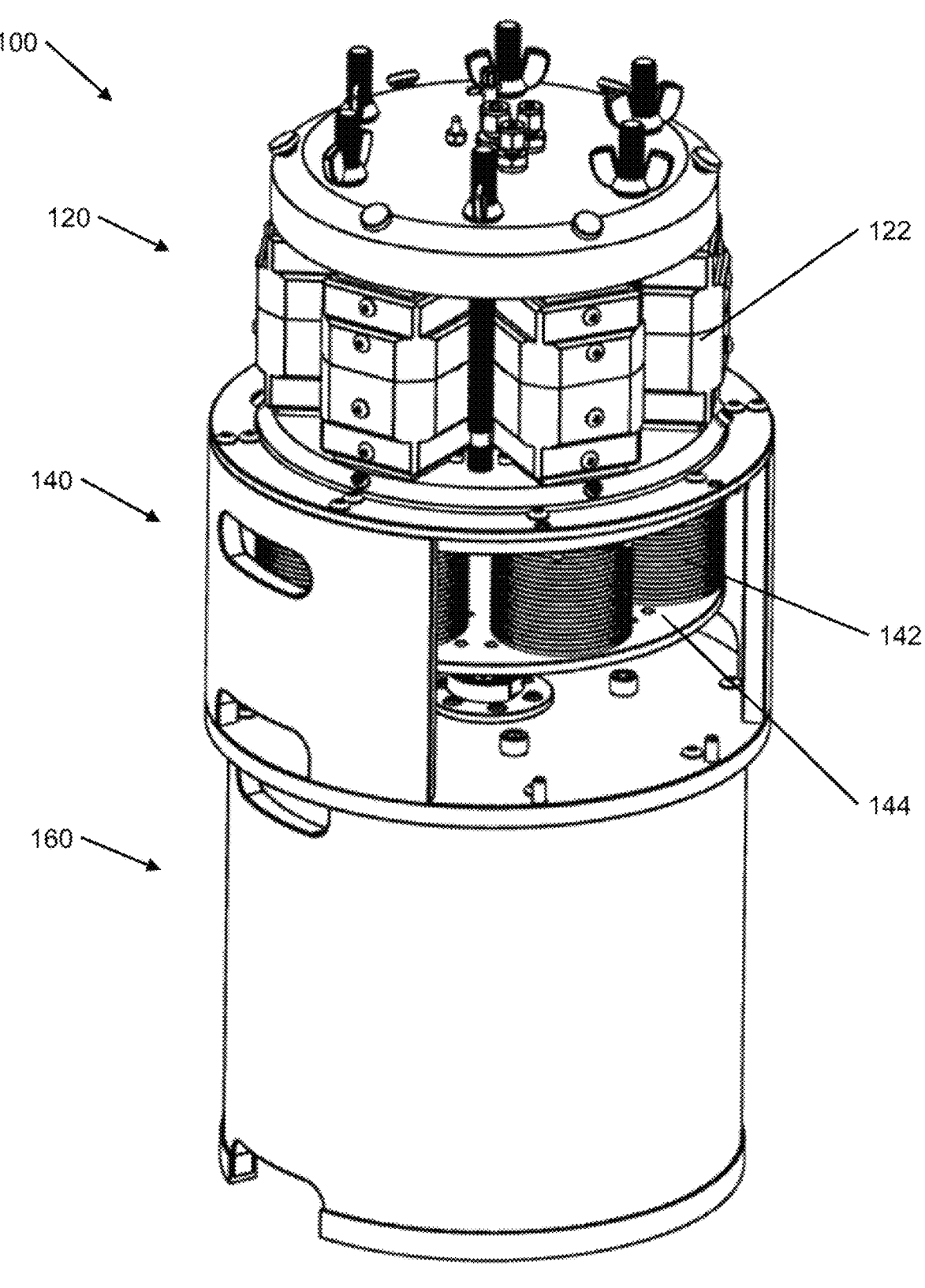
FIG. 2 is another upper, perspective view of the durability tester component with an open panel showing a pump unit of the durability tester component of the present invention.
Figure 3:
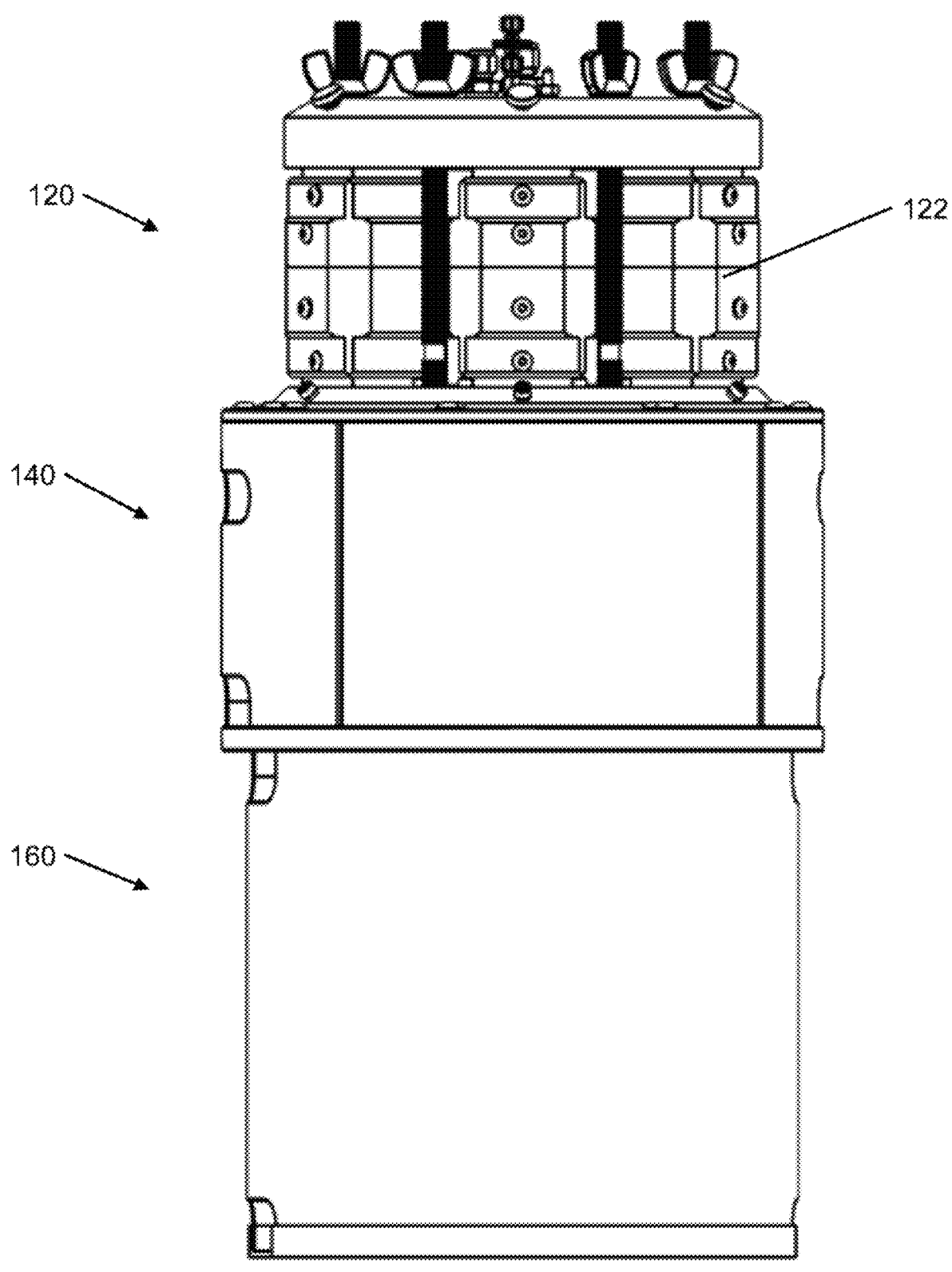
FIG. 3 is a front, elevational view of the durability tester component.
Figure 4:
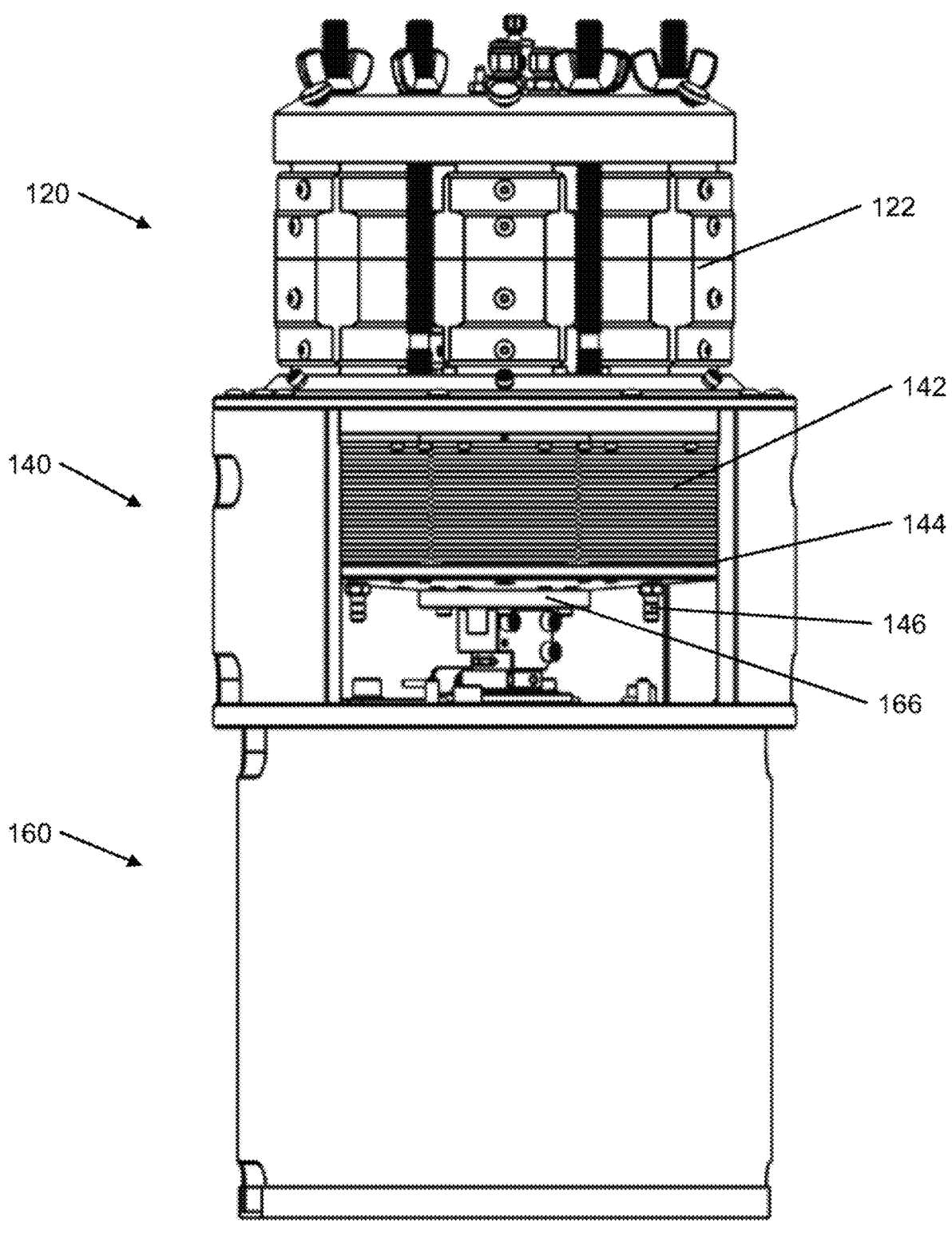
FIG. 4 is a back, elevational view of the durability tester component with an open panel showing aspects of the pump unit.
Figure 5:
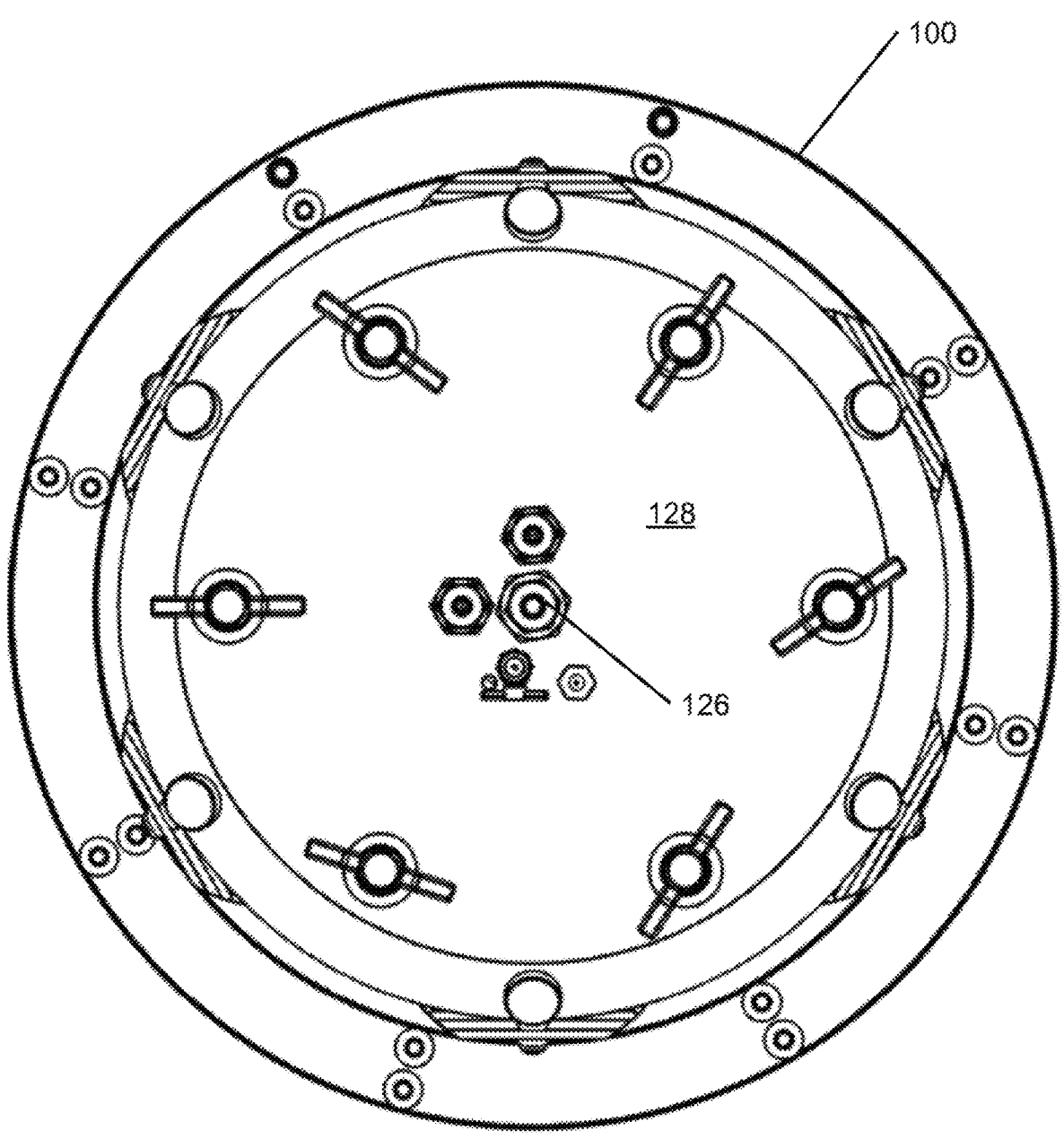
FIG. 5 is a top, plan view of the durability tester component.
Figure 6:
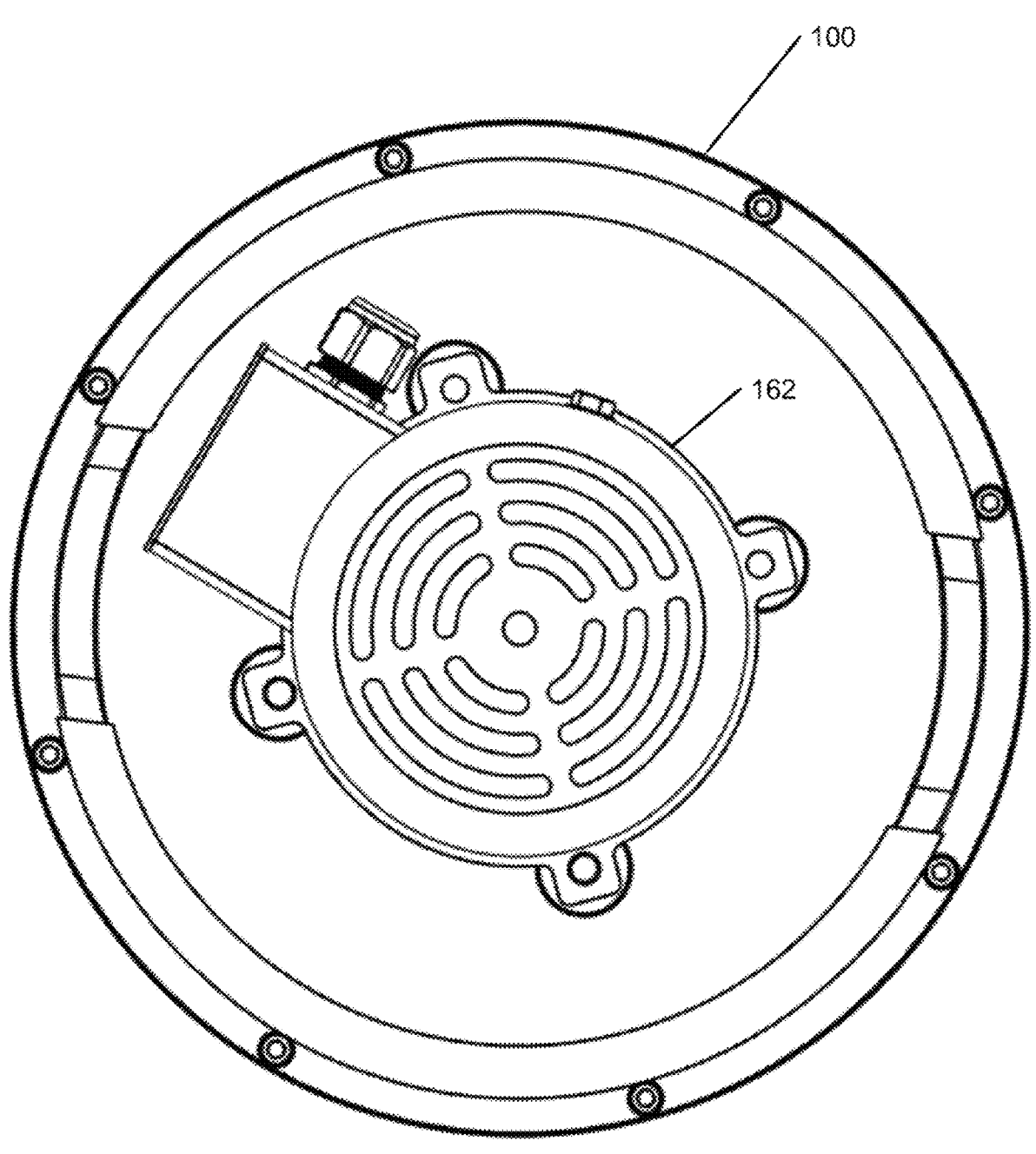
FIG. 6 is a bottom, plan view of the durability tester component.
Figure 7:
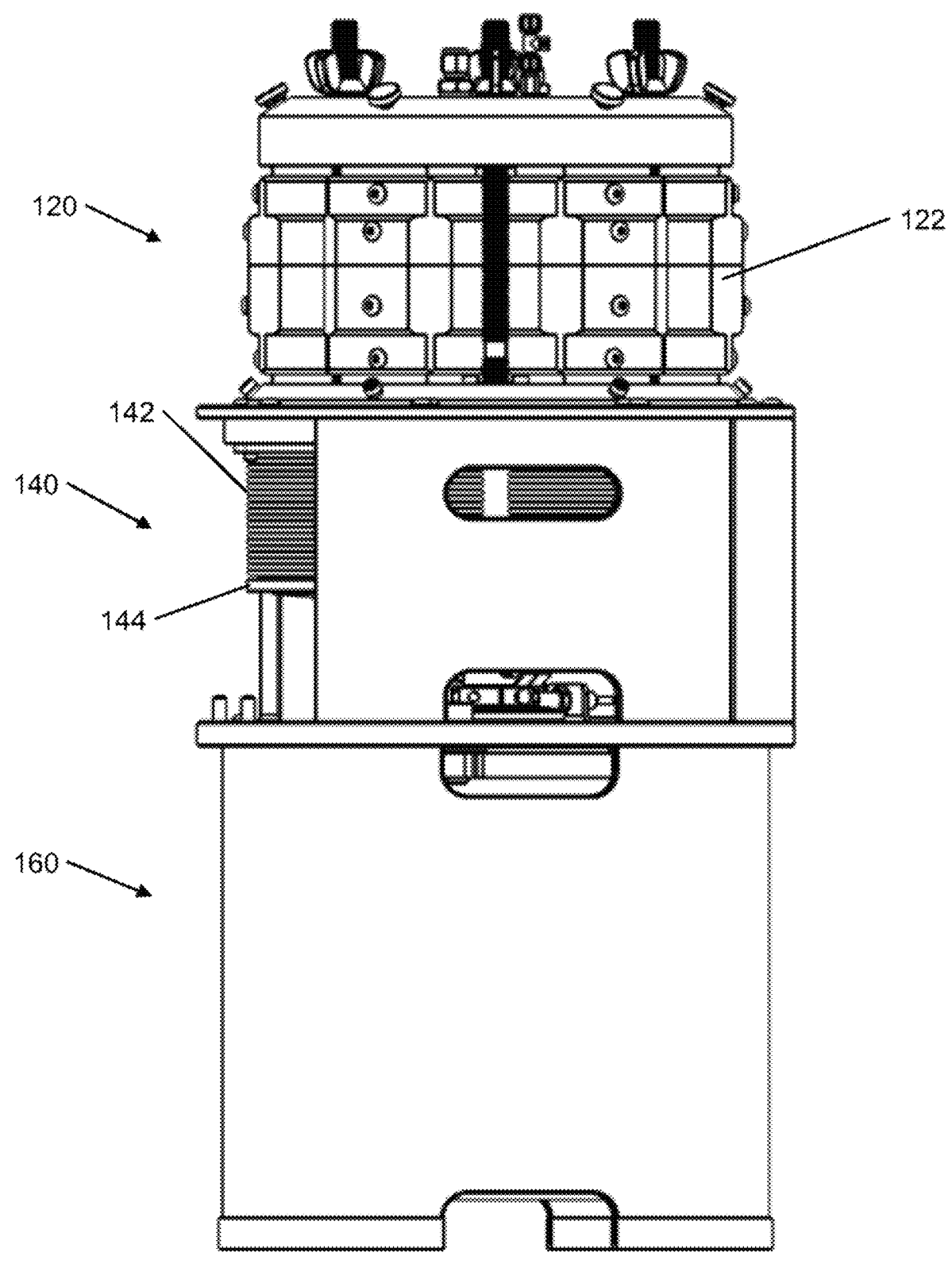
FIG. 7 is a side, elevational view of the durability tester component.
Figure 8:
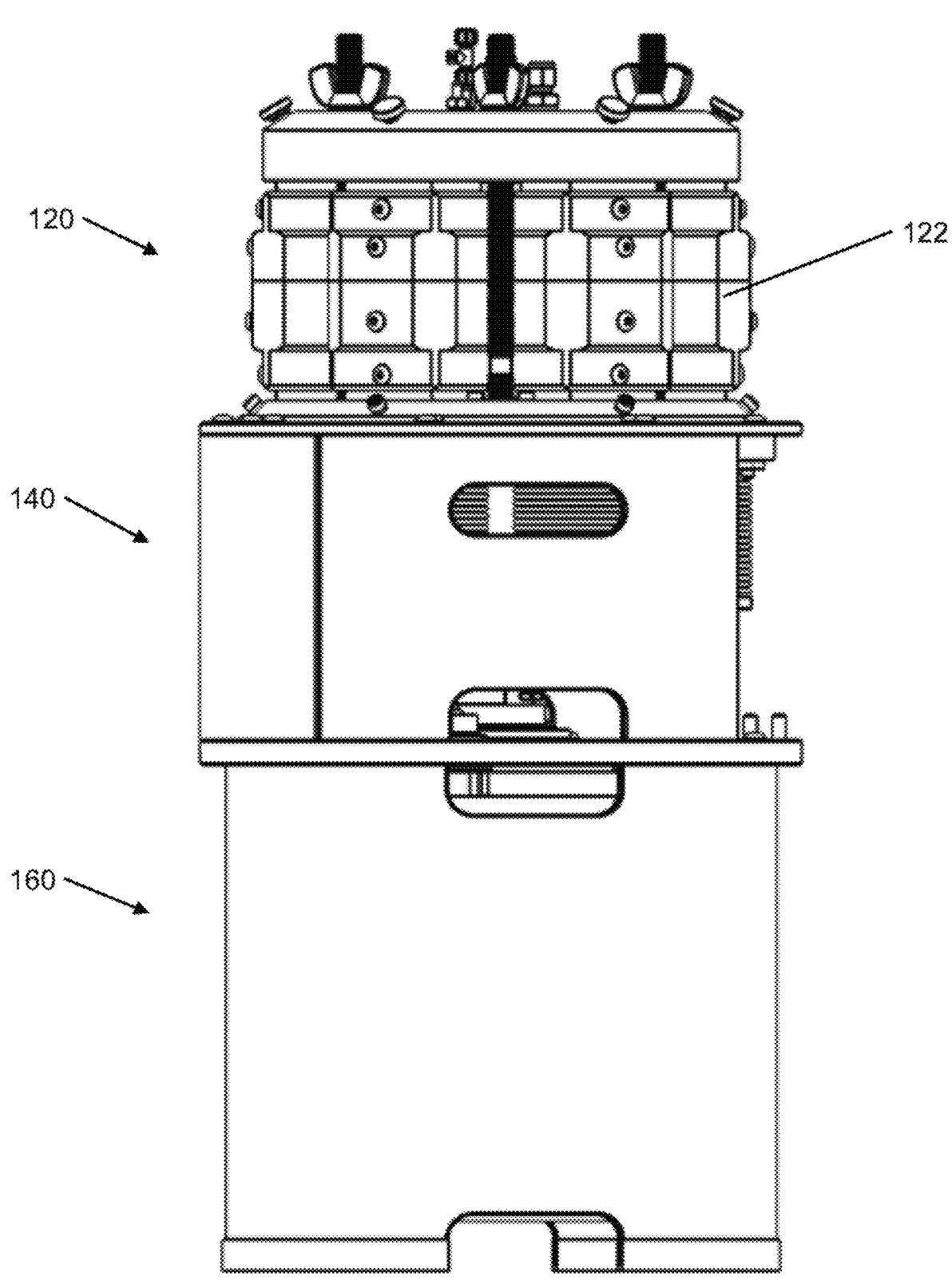
FIG. 8 is another side, elevational view of the durability tester component.
Figure 9:
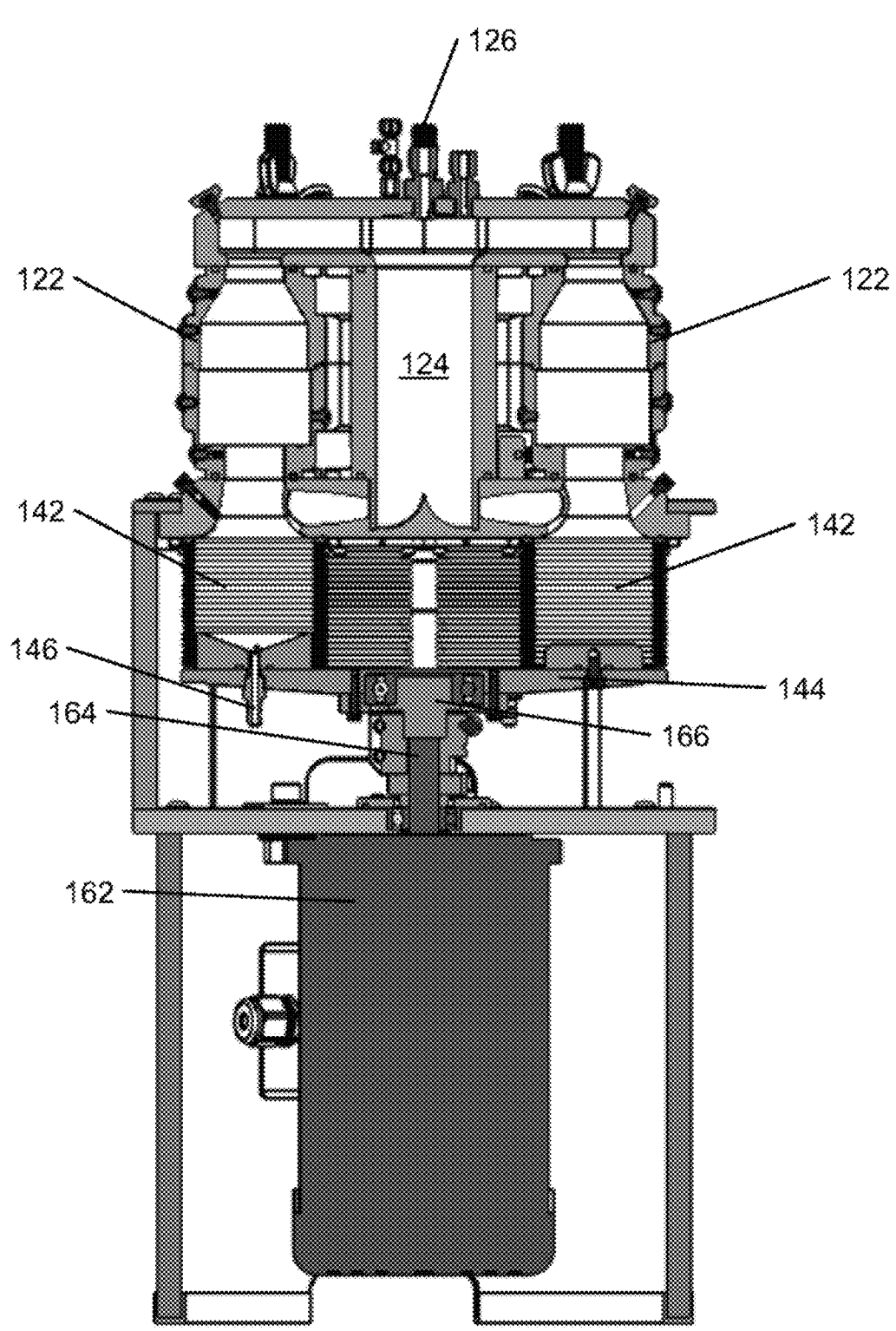
FIG. 9 is an elevational, cross-sectional view of the durability tester component showing aspects of the tester unit, the pump unit, and the drive unit of the durability tester component.

The drawing figures do not limit the present invention to the specific embodiments disclosed and described herein. The drawings are not necessarily to scale, emphasis instead being placed upon illustrating the principles of the invention.

DETAILED DESCRIPTION OF THE PREFERRED EMBODIMENTS

As required, a detailed embodiment of the present invention is disclosed herein; however, it is to be understood that the disclosed embodiment is merely exemplary of the principles of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The present invention comprises a medical device durability and particulate testing system 10 and method. In an exemplary embodiment, the durability and particulate testing system 10 of the present invention is configured for testing structural heart devices. In an exemplary embodiment, the present invention is configured for testing synthetic heart valves. In further embodiments, the present invention is configured for testing occluders, defect closure devices, candidate materials, surgical accessory devices, stents, shunts, other endovascular devices, and combinations thereof. In embodiments, the present invention is configured for testing multiple heart devices at one time. In an exemplary embodiment, the present system 10 is configured for testing three heart devices at one time. In an alternative embodiment, the present invention is configured for testing a single heart device. Embodiments of the present invention include devices for testing one, two, three, four, five, six, seven, eight, nine, 10, 11, 12, 13, 14, 15, or 16 structural heart device(s) at one time.

Figure 10:
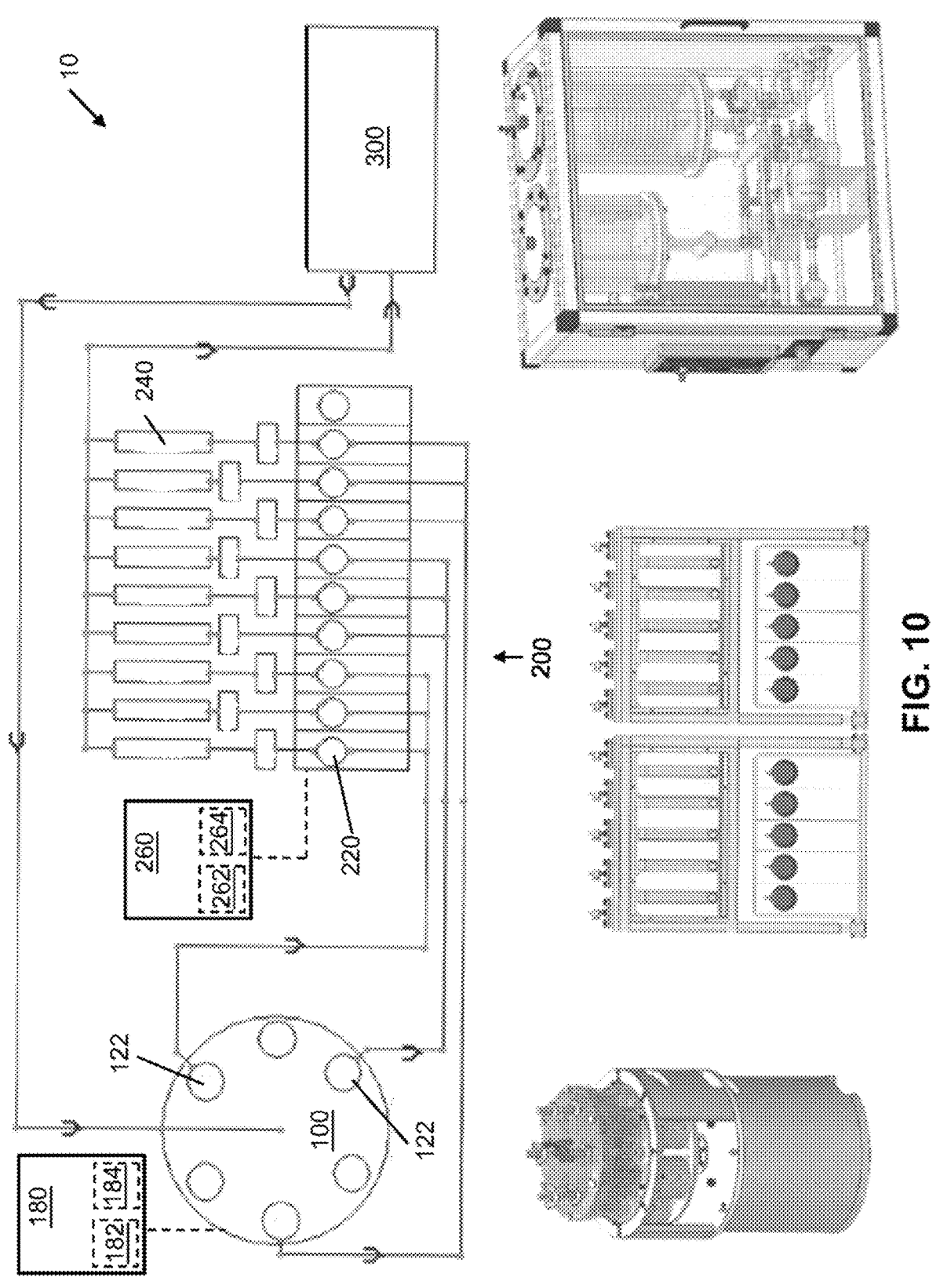
FIG. 10 shows a schematic drawing of a durability and particulate testing system embodying the present invention.

In an exemplary embodiment of the present invention, the durability and particulate testing system 10 includes a device durability tester component 100 configured for continually actuating movement of the medical device(s) being tested; a simulated blood fluid; fluid flow lines; a particulate counting component 200 comprising a series of particle counters 220 and configured for recording continuous particulate data from the medical device(s) subjected to durability testing; flow meters 240 to provide proper flow rates; a fluid management system 300; and one or more system controllers 180, 260 each having a processor 182, 262 configured with software for controlling operation of the system and recording data. In an exemplary embodiment, the present system comprises two controllers. A first controller comprises a durability testing computer 180 having a processor 182 configured for controlling operation of fluid flow and operation of the durability tester component 100. A second controller comprises a particulate counting computer 260 having a processor 262 configured for recording particulate counting and sizing data. In an alternative embodiment, one system controller is configured for controlling fluid flow, operation of the durability tester component, and recording particulate counting and sizing data. In an exemplary embodiment, the system controller(s) 180, 260 further include memory 184, 264 for storing data. Referring to the drawings, FIG. 10 shows a schematic drawing of an exemplary embodiment of a durability and particulate testing system 10 of the present invention and views of a durability tester component 100, a particulate counting component 200, and a fluid management system component 300.

In embodiments, the system 10 further includes one or more displays and one or more user interfaces accessible to user(s) via the display(s) and configured for displaying data and for allowing user(s) to customize operation of the system 10. In an embodiment, a first user interface is accessible via a display connected to a durability tester computer 180, and a second user interface is accessible via another display connected to a particulate counting computer 260. In such embodiments, the first user interface displays information regarding fluid flow and/or operation parameters of the durability tester component 100 of the invention and allows a user to customize operation of the system. Moreover, in this embodiment, the second user interface displays information regarding particulate counting and sizing data. In alternative embodiments, the present system includes a single user interface, which in some embodiments has multiple viewable screens, configured for displaying fluid flow, operation parameters, and particulate counting and sizing information, among other information about the system.

In some embodiments the system further includes one or more heaters paired with temperature measuring sensors to maintain fluid temperatures within appropriate bounds to simulate blood within the body during testing. In embodiments, the simulated blood fluid is maintained between 95 degrees and 105 degrees Fahrenheit; between 96 and 104 degrees Fahrenheit; between 97 and 103 degrees Fahrenheit; between 97 and 102 degrees Fahrenheit; between 97 and 101 degrees Fahrenheit; between 97 and 100 degrees Fahrenheit; between 98 and 99 degrees Fahrenheit; about 98.6 degrees Fahrenheit; about 97 degrees Fahrenheit; about 98 degrees Fahrenheit; about 99 degrees Fahrenheit; about 100 degrees Fahrenheit; about 101 degrees Fahrenheit; about 102 degrees Fahrenheit; or about 103 degrees Fahrenheit.

Additionally, in an exemplary embodiment, a pressure pump paired with pressure measuring devices are utilized to subject the test system to user desired pressure parameters. Preferably, the system controller(s) of the present invention, along with software programmed thereon, are configured to control a series of functions including but not limited to operation of motor(s), temperature control, pressure commands, alarm monitoring, and data collection.

FIGS. 1-9 show views of an exemplary embodiment of a device durability tester component 100 of the durability and particulate tester system 10 of the present invention. In an embodiment, the device durability tester component 100 is generally cylindrical in shape, but nevertheless, in other embodiments a durability tester component of the present invention can form an alternative general shape. In this embodiment, the device durability tester component comprises a test unit 120, a pump unit 140, and a drive unit 160.

In an exemplary embodiment, the test unit 120 comprises a series of medical device testing chambers 122 arranged in a substantially circular pattern around a central fluid reservoir 124. In alternative embodiments, testing chambers of the present invention are arranged around a central reservoir in an alternative pattern, such as but not limited to a triangular pattern, a square pattern, a rectangular pattern, a pentagonal pattern, a hexagonal pattern, an oval-shaped pattern, a line, or any other arrangement. In further embodiments, the test unit only includes one testing chamber. In some embodiments, the testing unit does not include a central reservoir and instead includes individual fluid inflow lines directly into each testing chamber.

In an exemplary embodiment, the central reservoir 124 is formed from a sealed connection between a throttle valve 125 and a test unit sealed top enclosure 128. In an exemplary embodiment, the test unit 120 includes openings from the central reservoir 124 into an upper opening into each testing chamber 122. In some embodiments, the openings into the upper portions of testing chambers can be selectively open or closed as desired by a user.

Figure 11:
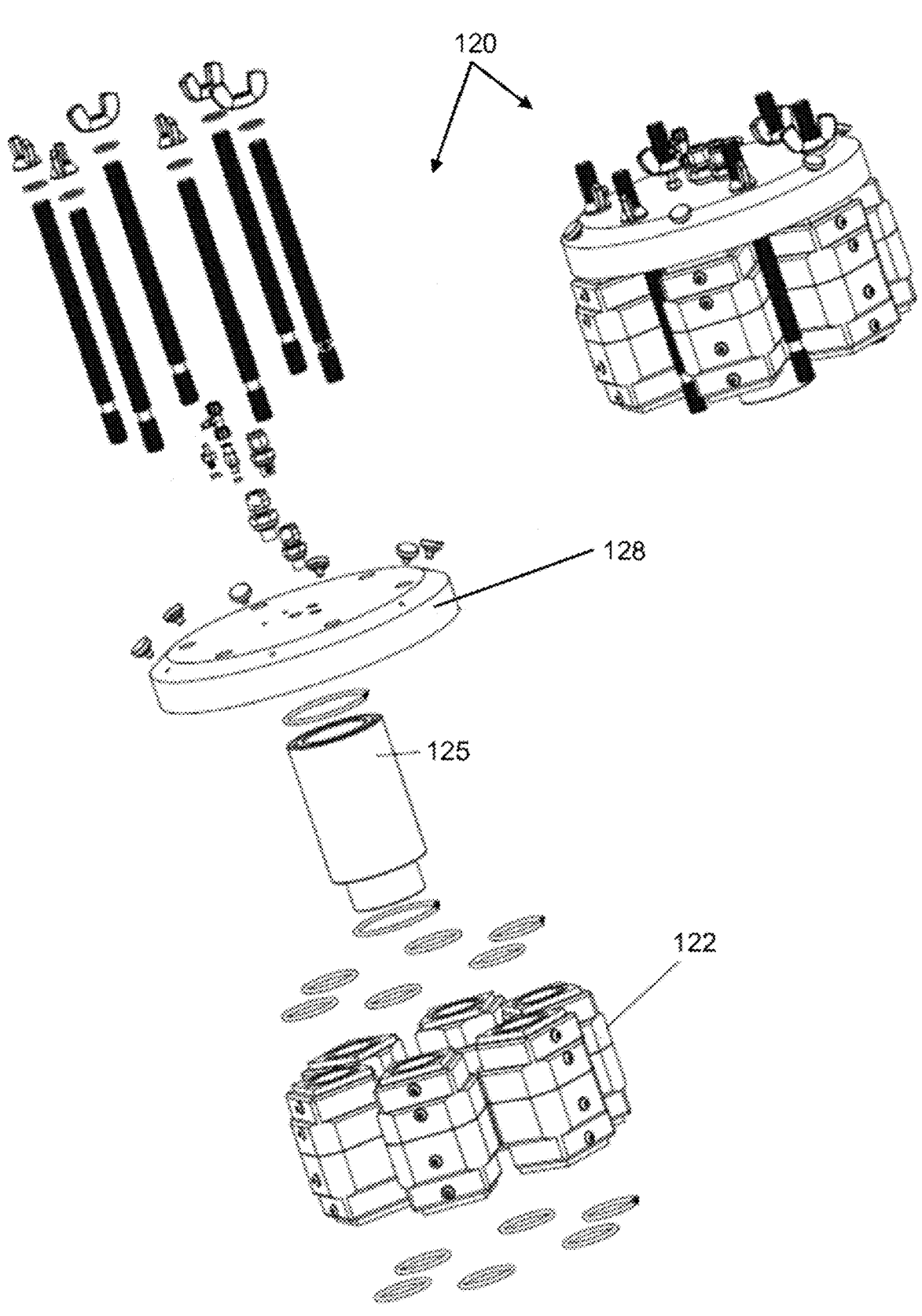
FIG. 11 shows an upper, perspective, assembled view and an upper, perspective, exploded view of a testing component of a durability tester component of the present invention.

In a preferred embodiment, connections between fluid-holding parts of the durability and particulate testing system 10 comprise sealed connections, including O-rings made of rubber or soft, sealable plastic(s) and/or other sealable fasteners. In an exemplary embodiment, the test unit 120 includes one or more fluid inflow line(s) 126 into the central fluid reservoir 124. In an exemplary embodiment, the fluid inflow line(s) 126 includes a luer lock connection to the test unit top enclosure 128. Nevertheless, in alternative embodiments, the fluid inflow line(s) connect to the test unit via sealed threading connection, articulated attachment, or any other type of sealed connection. In exemplary embodiments, the testing chambers 122; test unit top enclosure 128; and/or throttle valve are all or partially transparent or translucent to allow a user to view actuation of the devices within the testing chambers 122. FIG. 11 shows a perspective, exploded view and a perspective, assembled view of the test unit 120.

Figure 12:
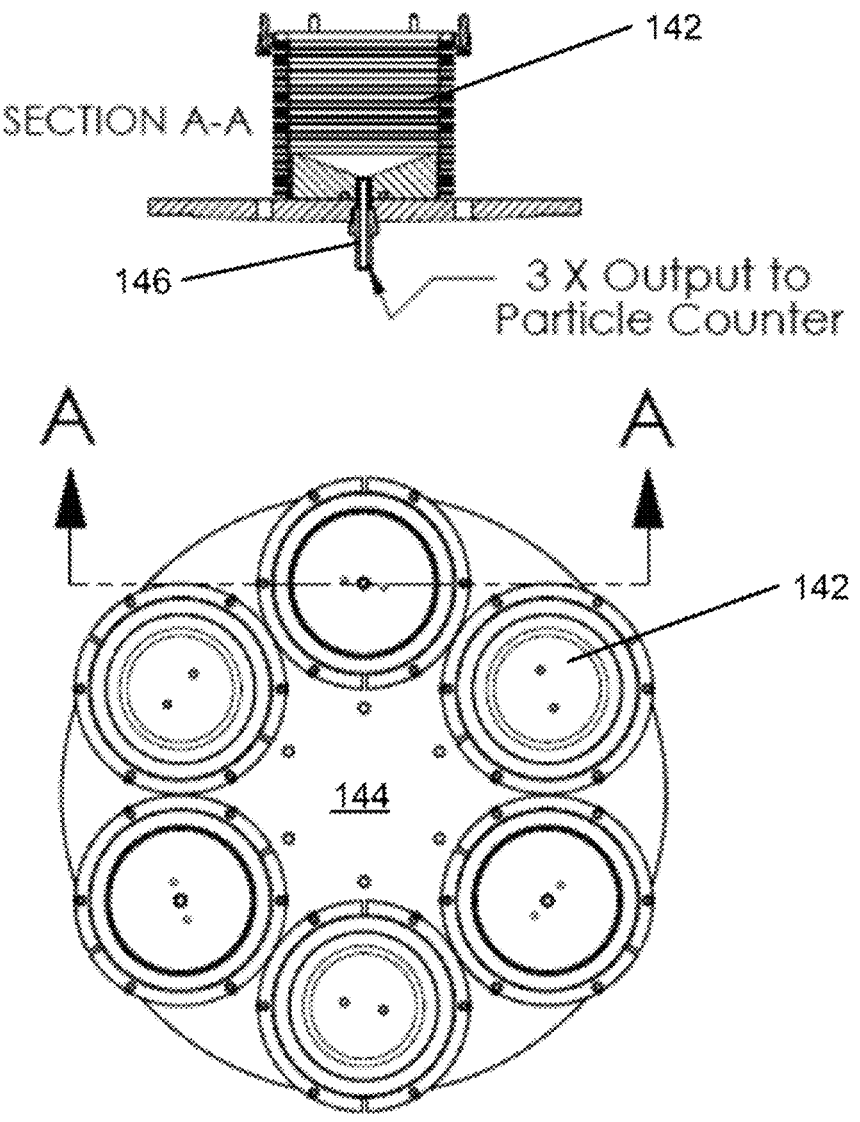
FIG. 12 shows a plan view of a pump unit of a durability tester component of the present invention and an elevational, cross-sectional view through a bellows of the pump unit.
Figure 13:
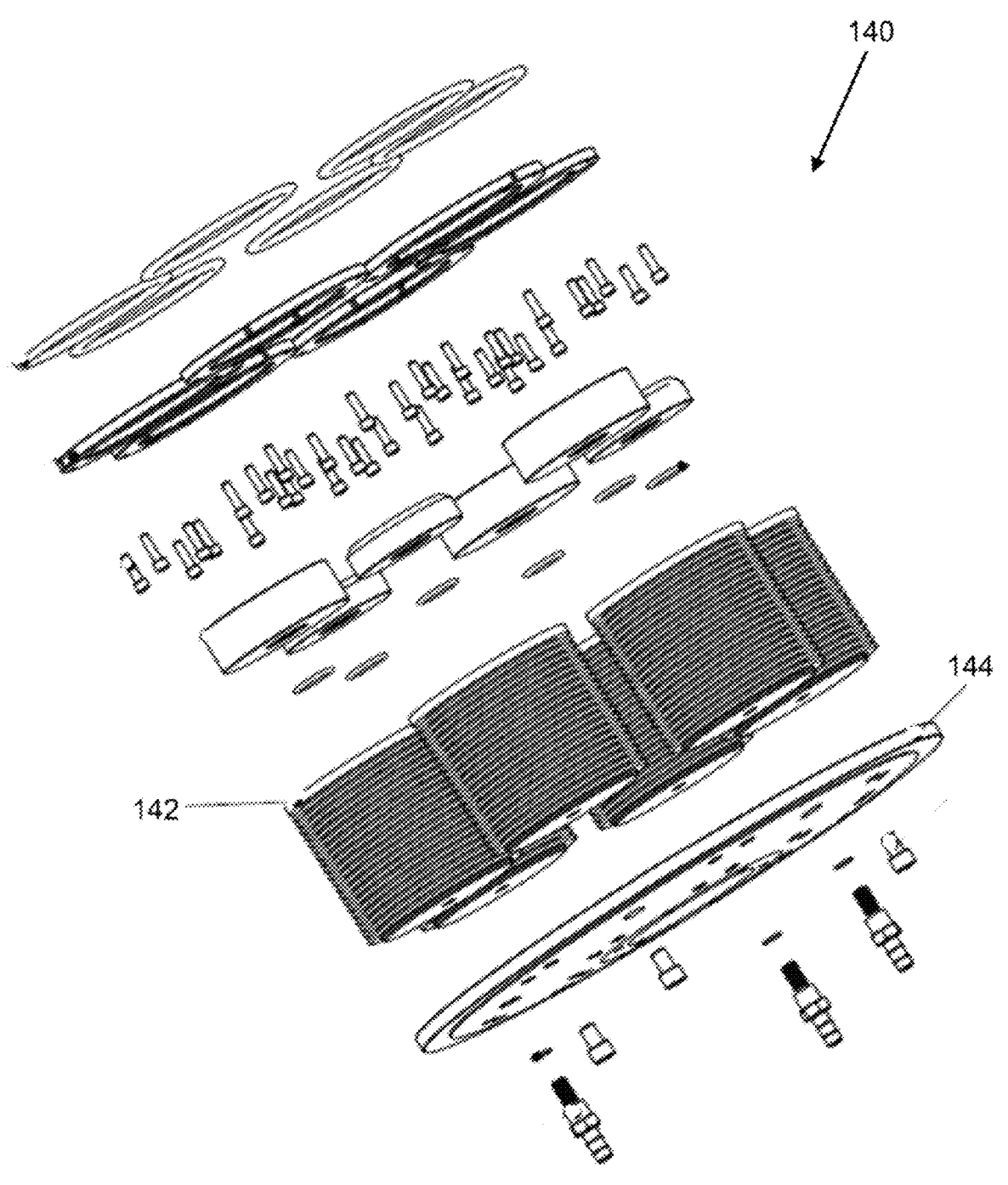
FIG. 13 is a lower, perspective, exploded view of a pump unit of a durability tester component of the present invention.

In an exemplary embodiment, the pump unit 140 comprises a series of bellows 142, which are sealedly connected to the base of the testing chambers 122. In an exemplary embodiment, the pump unit 140 includes a bellows 142 for each testing chamber 122 of the test unit 120. The bellows 142 of the present invention are configured to be compressed and expanded depending on pressure applied to the bellows 142. In an exemplary embodiment, the bellows 142 are attached to a pivotable, swash plate 144. In an embodiment, the swash plate 144 is substantially disc-shaped. Nevertheless, in embodiments in which the durability tester component is not substantially cylindrical, the shape of the swash plate corresponds to the arrangement of the testing chambers and bellows. In an exemplary embodiment, the pump unit 140 further includes outflow fluid lines 146 through the base of each bellows 142 and through the swash plate 144 to the particulate counting component 200. FIGS. 12 and 13 show plan; cross-sectional, elevational; and perspective, exploded views of the pump unit 140. As discussed above, in an exemplary embodiment, connections between fluid-holding parts of the pump unit and test unit comprise sealed connections, including O-rings made of rubber or soft, sealable plastic(s) and/or other sealable fasteners.

In an exemplary embodiment of the present invention, the drive unit 160 of the durability tester component 100 includes a motor 162 configured for connection to a power source and including a rotating rod 164 positioned below the swash plate 144 of the pump unit 140. The motor rotating rod 164 engages with the base of the pump unit swash plate 144 via a slanted coupling 166. The rotation of the rod 164 and the slanted coupling 166 is configured for tilting the swash plate 144 in a circular, or oscillating, motion without actual rotation of the swash plate 144.

Such tilting of the swash plate 144 with the motor 162 rotating the rotating rod 164 provides for alternating compression and expansion of the bellows 144 in a generally circular pattern (without twisting of the outflow lines 146, as would occur if the swash plate 144 were actually rotated). In an exemplary embodiment, this configuration of circumferential testing chambers, bellows, central fluid reservoir, swash plate, coupling, and motor is similar to the configuration of such features in the device shown in U.S. Pat. No. 4,546,642, the entirety of which is incorporated herein by reference, but with modifications and improvements made thereto.

In contrast to the device shown in U.S. Pat. No. 4,546,642, the present invention does not include bypass valves for directing fluid back into the central fluid reservoir from the testing chambers. Additionally, the present system includes one or more inflow fluid line 126 into the central fluid reservoir 124 and one or more outflow fluid line 146 from each bellows.

Figure 14:
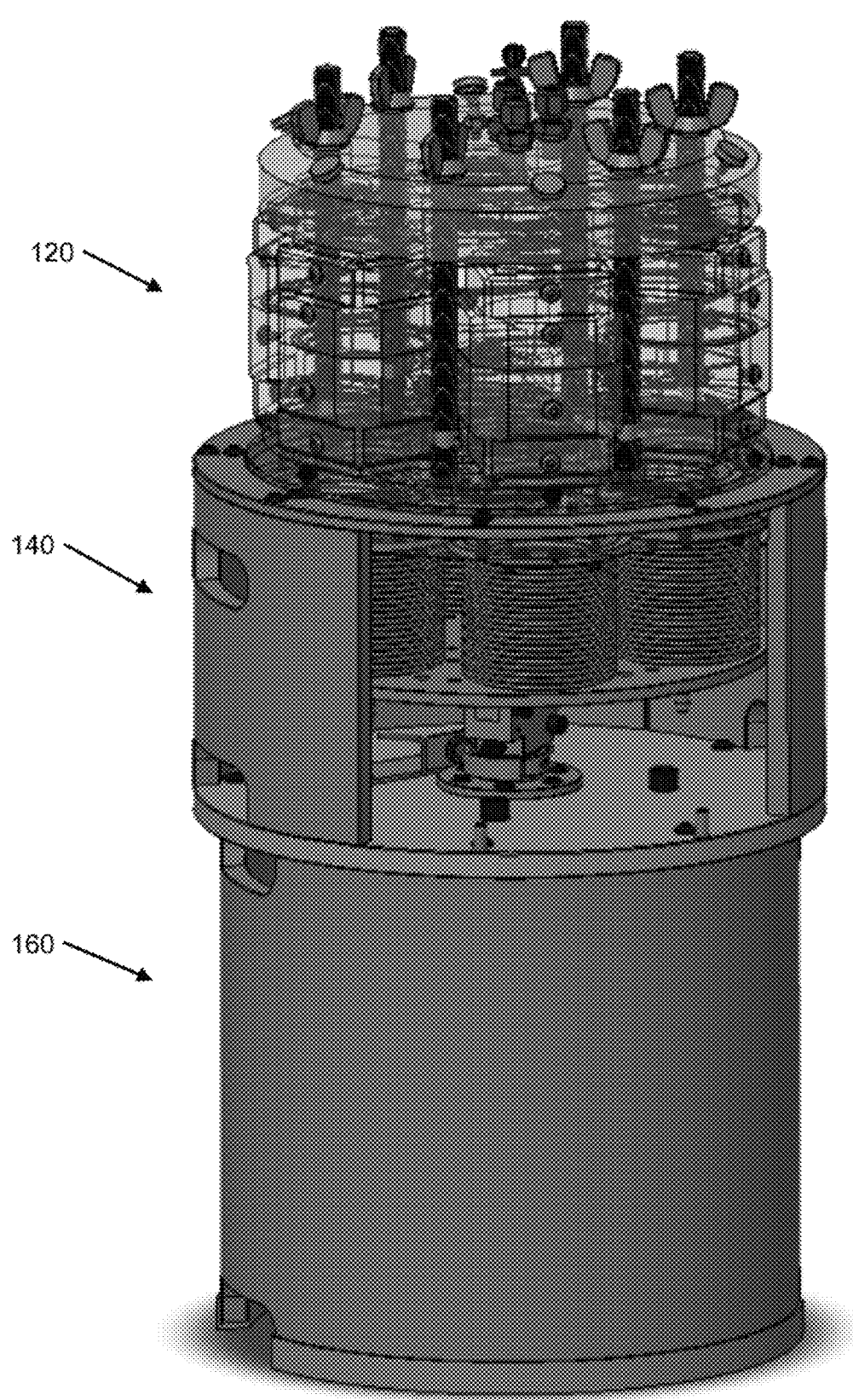
FIG. 14 is an upper, perspective view of an embodiment of a durability tester component of the present invention.
Figure 15:
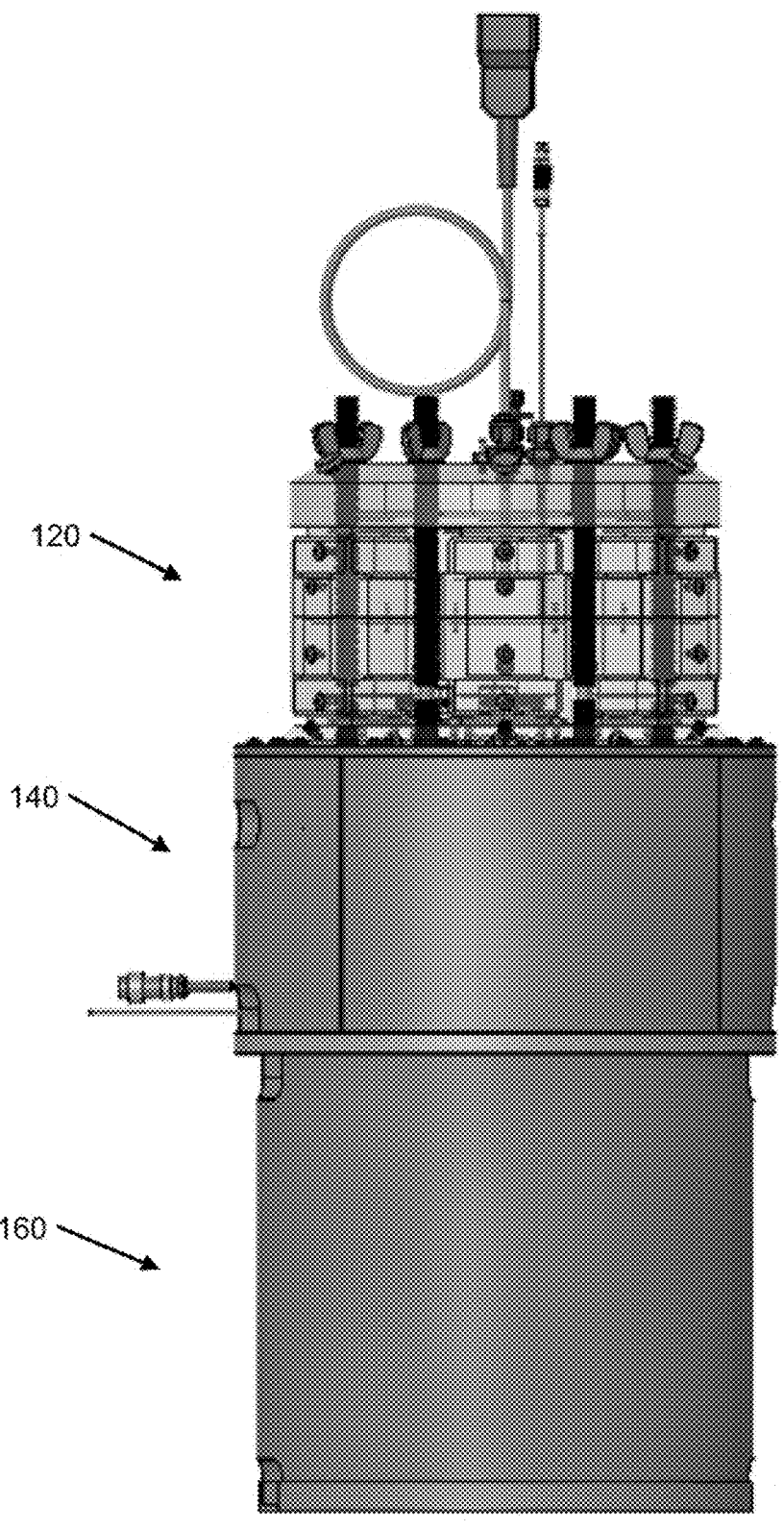
FIG. 15 is a front, elevational view of an embodiment of a durability tester component of the present invention with inflow and outflow fluid lines and a heater shown.
Figure 16:
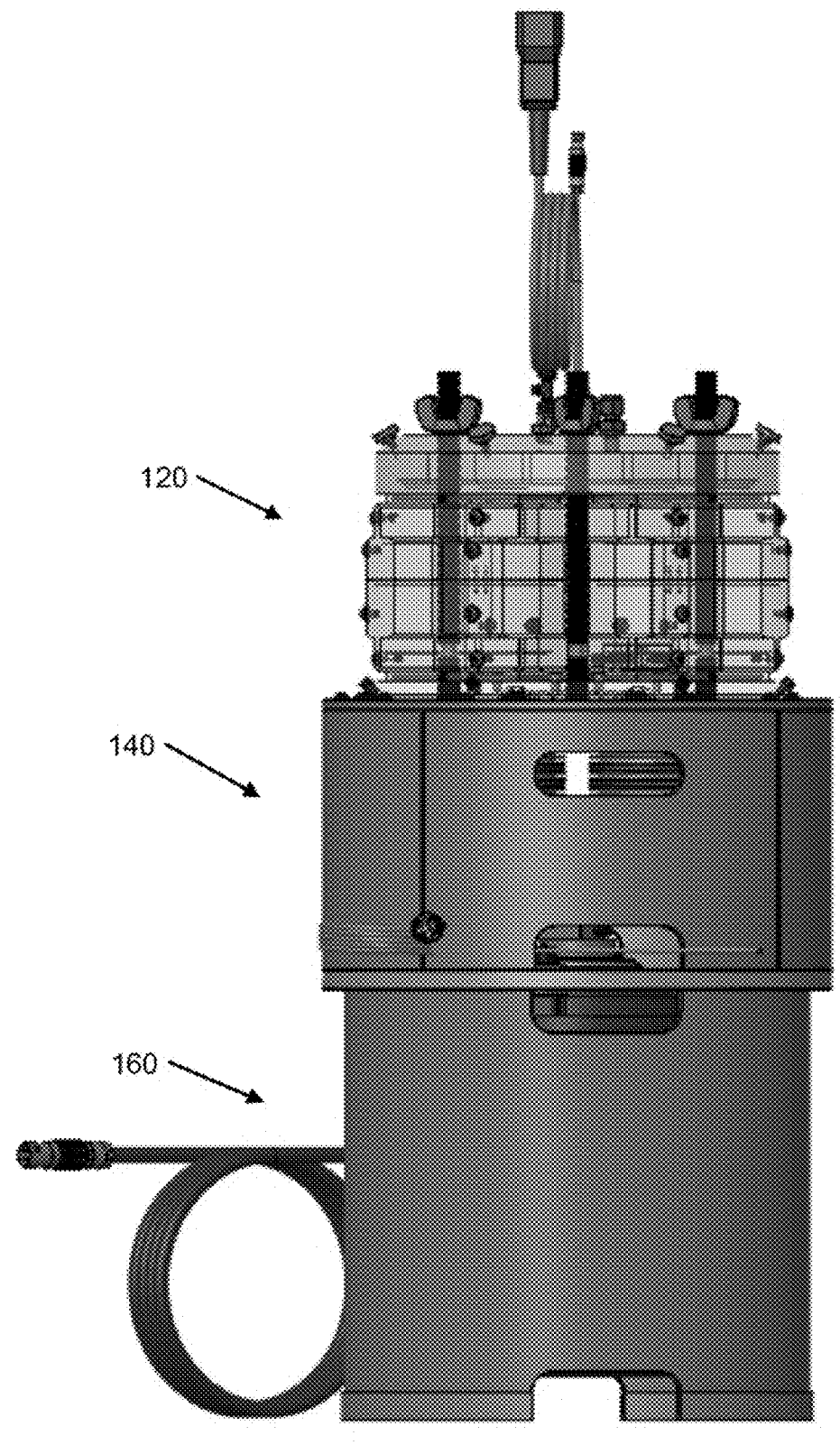
FIG. 16 is a side, elevational view of an embodiment of a durability tester component of the present invention with inflow and outflow fluid lines, a heater, and a power connection cord shown.

FIGS. 14-16 show views of an embodiment of the durability tester component 100 of the present durability and particulate tester system of the present invention. FIGS. 15 and 16 further illustrate fluid line, power line, heater, and sensor connections to and from the durability tester component 100 within the closed loop present system 10.

In an exemplary embodiment, the inflow fluid line 126 is configured to supply a continuous flow of simulated blood fluid from a fluid management system component 300 into the test unit central fluid reservoir 124 via one or more fluid management system pump(s). Outflow fluid lines 146 from the base of the bellows 142 are configured to direct fluid from the durability tester component 100 to a particle counting component 200 of the present invention. The lack of bypass valves in the test unit central fluid reservoir 124 and the inclusion of outflow fluid lines 146 at the base of each bellows 142 ensure that fluid which has passed through a medical device being tested within a testing chamber 122 is further directed toward the particle counting component 200 for accurate particle counting in line of the system 10. Moreover, individual outflow fluid lines 146 running from each of the bellows 142 below each testing chamber 122 accommodates specific and accurate particle counting and/or sizing from each testing chamber 122. Accordingly, in exemplary embodiments, the present system allows for multiple trials of the same device to be tested and/or multiple different devices to be tested at the same time.

In an exemplary embodiment of the present invention, simulated blood fluid is configured for being continuously pumped through the present system in a closed loop. Continuous tilting of the swash plate 144 and resulting alternating compression and expansion of the bellows 142 are configured to actuate movement of the medical devices within the testing chambers (e.g., repeatedly open and close synthetic heart valves) and simulate pulsatile flow of blood of the human circulatory system. In alternative embodiments, the flow of fluid from the fluid management system component through the rest of the system can be customized to be intermittent or pulsatile.

In exemplary embodiments of the present invention, the pressure and flow rate of fluid through the system can be varied to simulate implantation of the tested devices at different placements within the circulatory system and/or to speed up the timeframe to simulate the expected lifetime duration of the devices. In some embodiments, the outflow fluid lines are bifurcated, trifurcated, or further split between the outflow from durability tester component into the particulate counting component. Such splitting of fluid lines can be used to lower the pressure of the fluid flow into the particulate counting mechanism and/or to provide for more accurate particle counting. In an exemplary embodiment, the particulate counting component 200 comprises at least one particle counter 220 for every outflow line split. In an exemplary embodiment, the particulate counting component 200 further comprises flow meters 240 for controlling flow of fluid from the particle counters 220.

In exemplary embodiments, the present system can include a particle counting mechanism as disclosed within U.S. Pat. No. 7,621,192, the entirety of which is incorporated herein by reference; U.S. Pat. No. 9,453,788, the entirety of which is incorporated herein by reference; or any other type of particulate counter. Nevertheless, the particulate counting mechanism 200 of the present invention is in closed fluidic loop with the durability tester component 100 and the fluid management system component 300. In embodiments, the particulate counting component further includes laser counting and/or one or more particle filters.

In an exemplary embodiment, the fluid management system component 300 comprises one or more fluid reservoirs and one or more fluid pumps. In exemplary embodiments, the present system can include a fluid management system as disclosed within U.S. Pat. No. 7,621,192, the entirety of which is incorporated herein by reference; U.S. Pat. No. 9,453,788, the entirety of which is incorporated herein by reference; or any other type of fluid management system. Nevertheless, the fluid management system component 300 of the present invention is in closed fluidic loop with the durability tester component 100 and the particulate counting component 200. In an exemplary embodiment, the fluid management system component 300 further comprises one or more filters configured to filter out any remaining contaminants within the simulated blood fluid before recirculating the fluid through the durability tester component 100.

The present invention provides continuous particulate analysis of medical devices, such as structural heart devices, simultaneously undergoing durability testing. Particulate data are generated through the simulated (i.e., real-time or accelerated) life expectancy (or other specified time period) of the tested device(s). If degradation of a tested device does occur during the life expectancy of the device, the present system and method provides information regarding particulate count and size of particles released from the device, which data is useful to determine whether the device poses an embolic risk or other medical risk to a patient.

In an exemplary embodiment, many components of the present system are transparent or translucent, allowing a user to visualize operation of the device during testing. In an exemplary embodiment, testing chambers of the durability tester component are alternated for use and non-use to help prevent the potential for cross contamination.

In further embodiments, the durability and particulate testing component comprises capture filter housings for each particle counter lane. In an exemplary embodiment, the present system further includes cameras for regular visual monitoring of the testing. In further embodiments, the durability tester component includes individual fluid inflow lines into each testing chamber rather than a central fluid reservoir. In additional embodiments, the testing chambers, bellows, and outflow fluid lines are sectioned off from the other respective sections to prevent cross contamination.

In further embodiments, the present invention is configured for testing the durability and particulate shed of non-structural heart devices; other types of medical devices; veterinary medical devices; or other, non-medical devices, such as but not limited to pipe leak repair devices and vehicle repair devices, in place of structural heart devices.

Certain terminology is used in the description for convenience in reference only and will not be limiting. For example, up, down, front, back, right, and left refer to the invention as orientated in the view being referred to. The words "inwardly" and "outwardly" refer to directions toward and away from, respectively, the geometric center of the aspect being described and designated parts thereof. Forwardly and rearwardly are generally in reference to the direction of travel, if appropriate. Additionally, anatomical terms are given their usual meanings. For example, proximal means closer to the trunk of the body, and distal means further from the trunk of the body. Said terminology shall include the words specifically mentioned, derivatives thereof, and words of similar meaning.

As used in this specification and the appended claims, the singular forms "a", "an", and "the" include plural references unless the context clearly dictates otherwise. Thus, for example, a reference to "a method" includes one or more methods, elements, and/or steps of the type described herein and/or which will become apparent to those persons skilled in the art upon reading this disclosure and so forth.

As used in this specification and the appended claims, the use of the term "about" means a range of values including and within 15% above and below the named value, except for nominal temperature. For example, the phrase "about 3 mM" means within 15% of 3 mM, or 2.55-3.45, inclusive. Likewise, the phrase "about 3 millimeters (mm)" means 2.55 mm-3.45 mm, inclusive. When temperature is used to denote change, the term "about" means a range of values including and within 15% above and below the named value. For example, "about 5° C.," when used to denote a change such as in "a thermal resolution of better than 5° C. across 3 mm," means within 15% of 5° C., or 4.25° C.-5.75° C. When referring to nominal temperature, such as "about-50° C. to about +50° C.," the term "about" means+5° C. Thus, for example, the phrase "about 37° C." means 32° C.-42° C.

Unless defined otherwise, all technical and scientific terms used herein have the same meaning as commonly understood by one of ordinary skill in the art to which this invention belongs. Although any systems, elements, methods and materials similar or equivalent to those described herein can be used in the practice or testing of the present invention, the preferred systems, elements, and methods and materials are now described. All publications mentioned herein are incorporated herein by reference to describe in their entirety.

"Substantially" means to be more-or-less conforming to the particular dimension, range, shape, concept, or other aspect modified by the term, such that a feature or component need not conform exactly. For example, a "substantially cylindrical" object means that the object resembles a cylinder but may have one or more deviations from a true cylinder. "Comprising," "including," and "having" (and conjugations thereof) are used interchangeably to mean including but not necessarily limited to, and are open-ended terms not intended to exclude additional, unrecited elements or method steps.

Changes may be made in the above methods, devices and structures without departing from the scope hereof. Many different arrangements of the various components depicted, as well as components not shown, are possible without departing from the spirit and scope of the present invention. Embodiments of the present invention have been described with the intent to be illustrative and exemplary of the invention, rather than restrictive or limiting of the scope thereof. Alternative embodiments will become apparent to those skilled in the art that do not depart from its scope. Specific structural and functional details disclosed herein are not to be interpreted as limiting, but merely as a representative basis for teaching one of skill in the art to employ the present invention in any appropriately detailed structure. A skilled artisan may develop alternative means of implementing the aforementioned improvements without departing from the scope of the present invention.

The foregoing and other objects are intended to be illustrative of the invention and are not meant in a limiting sense. Many possible embodiments of the invention may be made and will be readily evident upon a study of the following specification and accompanying drawings comprising a part thereof. Various features and subcombinations of invention may be employed without reference to other features and subcombinations. Other objects and advantages of this invention will become apparent from the following description taken in connection with the accompanying drawings, wherein is set forth by way of illustration and example, an embodiment of this invention and various features thereof.

It is also to be understood that the following claims are intended to cover all of the generic and specific features of the invention herein described, and all statements of the scope of the invention which, as a matter of language, might be said to fall therebetween.

Having thus described the invention, what is claimed as new and desired to be secured by Letters Patent is:

1. A medical device durability and particulate tester system comprising:
    a durability tester component fluidically connected to a particulate counting component and a fluid management component;
    a simulated blood fluid for circulation through said system;
    said durability tester component comprising one or more testing chambers each configured for selectively housing a medical device to be tested;
    said one or more testing chambers fluidically connected to said fluid management component via a fluid inflow line;
    said durability tester component further comprising one or more compressible bellows each fluidically connected to one of said testing chambers;
    each said bellows attached to a pivotable swash plate;
    a drive motor having a rotatable rod, said rod comprising a coupling configured for engaging with said swash plate such that rotation of said rod tilts said swash plate in an oscillating pattern;
    wherein said tilting of said swash plate is configured for alternatingly compressing and expanding said one or more bellows;
    wherein said alternating compression and expansion of said one or more bellows is configured for actuating said medical device within each said testing chamber;
    each said bellows comprising a fluid outflow line to said particulate counting component;
    wherein said particulate counting component is configured for counting particles within fluid downstream of said one or more testing chambers;

said fluid management component comprising a fluid pump;
    a controller having a processor configured for controlling actuation of said motor and said fluid pump; and
    wherein said system is configured for continuous flow of simulated blood fluid through said system and simultaneously testing durability and particulate shed of said medical device within each said testing chamber for a simulated expected use time frame for said medical device.

2. The system of claim 1, wherein:
    said durability tester component comprises multiple testing chambers and an equal number of bellows as said testing chambers.

3. The system of claim 2, wherein:
    said multiple testing chambers comprises three testing chambers; and
    said equal number of bellows as said testing chambers comprises three bellows.

4. The system of claim 2, wherein:
    said durability tester component further comprises a central fluid reservoir fluidically connected to each said testing chamber; and
    said fluid inflow line is configured to supply simulated blood fluid into said central fluid reservoir.

5. The system of claim 4, wherein:
    said central fluid reservoir comprises a throttle valve sealingly connected to a top enclosure.

6. The system of claim 1, wherein:
    said particulate counting component comprises a particle counter for each fluid outflow line.

7. The system of claim 6, wherein:
    said fluid outflow lines are bifurcated.

8. The system of claim 6, wherein:
    said fluid outflow lines are trifurcated.

9. The system of claim 1, wherein:
    said particulate counting component further comprises flow meters.

10. The system of claim 1, further comprising:
    a particle counting computer having a processor programmed with software for recording particulate counting data.

11. The system of claim 10, wherein:
    said particle counting computer further comprising memory for storing said particle counting data.

12. The system of claim 10, wherein:
    a particle counting computer further comprising a display; and
    said system further comprising a user interface accessible via said display for reviewing said particulate counting data.

13. The system of claim 1, wherein:
    said controller comprises a system computer comprising a display; and
    said system further comprising a user interface accessible via said display for reviewing and selective adjustment of fluid flow and motor parameters of the system.

14. The system of claim 1, wherein:
    said one or more testing chambers are transparent.

15. The system of claim 1, wherein:
    said one or more testing chambers are translucent.

16. The system of claim 1, further comprising:
    a heater configured for heating said simulated blood fluid within the system to simulate blood temperature within the human body.

17. The system of claim 1, wherein:

said fluid management system further comprises a filter for filtering said simulated blood fluid prior to recirculation through said durability tester component.

18. A method of testing durability and particulate shed of a medical device, the method comprising the steps of:

providing a durability tester component fluidically connected to a particulate counting component and a fluid management component;

providing a simulated blood fluid;

wherein said durability tester component comprises one or more testing chambers fluidically connected to said fluid management component via a fluid inflow line;

wherein said durability tester component further comprises one or more compressible bellows each fluidically connected to one of said testing chambers;

wherein each said bellows is attached to a pivotable swash plate;

providing a drive motor having a rotatable rod, said rod comprising a coupling configured for engaging with said swash plate such that rotation of said rod tilts said swash plate in an oscillating pattern;

wherein each of said bellows comprises a fluid outflow line to said particulate counting component;

wherein said fluid management component comprises a fluid pump;

providing a controller having a processor configured for controlling actuation of said motor and said fluid pump;

placing a medical device within each of said testing chambers;

pumping said simulated blood fluid from said fluid management component into said one or more testing chambers via said fluid inflow line;

actuating said motor;

said motor tilting said swash plate in an oscillating pattern, alternatingly compressing and expanding said one or more bellows, and actuating said medical device;

said simulated blood fluid flowing from said one or more bellows to said particulate counting component via each said fluid outflow line;

said particulate counting component recording particulate counting data; and determining the durability and particulate shed of said medical device.

19. The method of claim 18, wherein:

said one or more testing chambers comprises three testing chambers; and said one or more bellows comprises three bellows.

20. The method of claim 18, further comprising the step of:

heating said simulated blood fluid to a temperature to simulate blood within a human body.

* * * * *